US006790457B1

(12) United States Patent
Brown et al.

(10) Patent No.: US 6,790,457 B1
(45) Date of Patent: Sep. 14, 2004

(54) COMPOSITIONS AND METHODS FOR REDUCING OR PREVENTING FERTILIZATION IN FISH AND BIRDS

(75) Inventors: Robert Brown, Dartmouth (CA); Bill Pohajdak, Dartmouth (CA); Janet Horrocks, Dundee (GB); Leslie McLaren, Truro (CA)

(73) Assignee: Dalhousie University, Halifax (CA)

( * ) Notice: Subject to any disclaimer, the term of this patent is extended or adjusted under 35 U.S.C. 154(b) by 0 days.

(21) Appl. No.: 09/868,983

(22) PCT Filed: Dec. 22, 1999

(86) PCT No.: PCT/CA99/01225

§ 371 (c)(1),
(2), (4) Date: Nov. 27, 2001

(87) PCT Pub. No.: WO00/37100

PCT Pub. Date: Jun. 29, 2000

Related U.S. Application Data (60) Provisional application No. 60/113,526, filed on Dec. 22, 1998.

(51) Int. Cl.$^7$ ............................................... A61K 9/127
(52) U.S. Cl. .................... 424/450; 424/278.1; 424/581; 514/841; 514/842
(58) Field of Search .............................. 424/450, 278.1, 424/581, 184.1; 514/841, 842

(56) References Cited

U.S. PATENT DOCUMENTS 5,910,568 A * 6/1999 Hammerstedt et al.

OTHER PUBLICATIONS

Brown, R.G. et al. (1997) "Evidence for a long–lasting single administration contraceptive vaccine in wild grey seals" J. Reprod. Immunol. 35:43–51.
New, Roger R.C. (1990) "Lipsomes: A practical approach" pp. 1–32 and 33–104.
Roberts, Jane and Tilzey, Richard (1996) "Controlling Carp: Exploring the options for Australia" 1997 SCIRO Publications 314 Albert Street, East Melbourne, Victoria, Australia, especially pp. 108–118.
Amanze, D. and Iyengar, A. (1990) "The micropyle: a sperm guidance system in teleost fertilization." Development 109:495–500.
Bakst, M.R. and Howarth, B. (1977) "Hydrolysis of hens perivitelline layer by cock sperm in vitro." Biol. Reproduct. 17:370–379.
Brown, R.G., Kimmins, W.C., Mezei, M., Parsons, J.L., Pohajdak, B. and Bowen, W.D. (1996) "Birth control for grey seals." Nature 379:30–31.
Chang, Y.S., Wang, S.C., Tsao, C.C. and Huang, F.L. (1996) "Molecular cloning, structural analysis and expression of carp.ZP3 gene." Mol.Reprod.Dev.44:295–304.
Chang, Y.S., Hsu, C.C., Wang; S.C., Tsao, C.C. and Huang, F.L. (1997) "Molecular cloning, structural analysis and expression of carp ZP2 gene." Mol.Reprod.Dev.46:258–67.
Epifano, O., Liang, L–F. and Dean, J. (1996) "Mouse ZP1 encodes a zona pellucida protein homologous to egg envelope proteins in mammals and fish." J.Biol.Chem.270: 27254–27258.
Hamazaki, T.S., Nagahama, Y. and Yamagami, K. (1989) "A glycoprotein from liver constitutes the inner layer of the egg envelope (zona pellucida interna) of the fish, *Oryzias latipes.*"Dev.Biol.133:101–110.

(List continued on next page.)

*Primary Examiner*—Gollamudi S. Kishore (57) ABSTRACT

Disclosed is an immunocontraceptive vaccine composition comprising a teleost homolog of zona pellucida (TH-ZP), together with a pharmaceutically acceptable diluent or carrier, for reducing or preventing fertilization in a fish, and a method for its use. Also disclosed is immunocontraceptive vaccine composition comprising an antigen from an inner perivitelline layer (IPVL), together with a pharmaceutically acceptable diluent or carrier, for reducing or preventing fertilization in a bird, and a method for its use.

22 Claims, 4 Drawing Sheets

OTHER PUBLICATIONS

Harris, J.D., Hibler, D.W., Fontenot, G.K., Hsu, K.T., Yurewicz, E.C. and Sacco, A.G.(1994) "Cloning and characterization of zona pellucida genes and cDNA's from a variety of mammalian species : the ZPA, ZPB and ZPC gene families DNA sequence." J. Sequencing and Mapping 4:361–393.

Herbinger, C.M., Doyle, R.W., Pitman, E.R., Paquet, D., Mesa, K.A., Morris, D.B., Wright, J.M. and Cook, D. (1995) DNA fingerprint based analysis of paternal and maternal effects on offspring growth and survival in communally reared rainbow trout. Aquaculture 137:245–256.

Hinds, Lyn A et al. "Immuno–contraceptive control for carp" 1997 Workshop; Albury South Wales, Australia; Oct. 22–24, 1996.

Hjerten, S et al. (1985) "Studies of fish zona pellucida by high–performance ion–exchange chromatography on agarose columns and free zone electrophoresis" Journal of Chromatography Biomedical Applications, vol. 341, pp. 295–304.

Jentoft, N. and Dearborn,D.G. (1979) "Labelling of proteins by reductive methylation using sodium cyanoborohydride." J.Biol.Chem.254:4359–4365.

Lyons, C.E., Payette, K.L., Price, J.L. and Huang, R.C.C.(1993) "Expression and structural analysis of a teleost homolog of a mammalian zona pellucida gene." J.Biol.Chem.268:21351–21358.

Mochida K et al: (1993) "Sperm Infertility caused by experimental testicular autoimmunity in the Nile Tilapia." Nippon Suisan Gakkaishi–Bulletin of the Japanese Society of Scientific Fisheries, (Feb. 1993) vol. 59, No. 2, pp. 253–261.

Murata, K. Sasaki, T., Yasumasu, S., Iuchi, I., Enami, J., Yasumasu, I. and Yamagami, K. (1995) "Cloning of cDNAs for the precursor protein of a low–molecular weight subunit of the inner layer of the egg envelope (chorion) of the fish *Oryzias latipes.*"

Murata, K., Sugiyama, H., Yasumasu, S., Iuchi, I., Yasumasu, I. And Yamagami, K. (1997) "Cloning of cDNA and estrogen–induced hepatic gene expression for chorigenin H, a precusor protein of the fish egg envelope (chorion)." Proc.Natl.Acad.Sci. USA 94:2050–2055.

Muttilaninen, S., Idanpaan–Heikkila, I., Wahlstrom, E., Nurminen, M., Makela, P.H. and Sarvas, M. (1995) "The *Neisseria meningitidis* outer membrane protein P1 produced in *Bacillus subtilis* and reconstituted into phospholipid vesicles elicits antibodies to native P1 epitopes." Microb. Pathog.18:423–436.

Robertson, L., Brown, H.L., Staines, H.J. and Wishart, G.J. (1997) "Characterization and application of an avian in vitro spermatozoa–egg interaction assay using the inner perivitelline layer from laid chicken eggs." J. Reproduct. Fertil. 110:205–211.

Taguchi, T., Seko, A., Kitajima, K., Muko, Y., Inoue, S., Knoo, K–H., Morris, H.R., Dell, A. and Inoue, Y.(1994) "Structural studies of a novel type of pentaantennary large glycan unit in the fertilization–associated carbohydrate–rich glycopeptide isolated from the fertilized eggs of *Oryzias latipes.*" J.Biol.Chem 269:8762–8771.

Tezuka, T., Taguchi, T., Kanamori, A., Muto, Y., Kitajima, K., Inoue, Y. and Inoue, S. (1994) "Identification and structural determination of the KDN–containing N–linked glycan chains consisting of bi– and triantennary complex–type units of KDN–glycoprotein previously isolated from rainbow trout vitelline envelopes." Biochem.33:6495–6502.

* cited by examiner

COMPOSITIONS AND METHODS FOR REDUCING OR PREVENTING FERTILIZATION IN FISH AND BIRDS

CROSS-REFERENCE TO RELATED APPLICATIONS

This application is the national phase of International Application No. PCT/CA99/01225, filed Dec. 22, 1999, and claims the benefit of U.S. Provisional Patent Application No. 60/113,526, filed Dec. 22, 1998.

FIELD OF THE INVENTION

The present invention relates to a vaccine composition for the immunocontraception of fish. The present invention also relates to a vaccine composition for the immunocontraception of birds.

BACKGROUND OF THE INVENTION

Among vertebrates, mating strategies involve behaviour, gamete structure and the specificity of recognition of sperm and egg. Mammalian oocytes are surrounded by an envelope called the zona pellucida that is composed of three glycoproteins in a ratio of 1:2:2 denoted by ZPA, ZPB, and ZPC (Harris, J. D., Hibler, D. W., Fontenot, G. K., Hsu, K. T., Yurewicz, E. C. and Sacco, A. G.(1994) "Cloning and characterization of zona pellucida genes and cDNA's from a variety of mammalian species: the ZPA, ZPB and ZPC gene families DNA sequence." J. Sequencing and Mapping 4:361–393). The zona pellucida contains species-specific sperm receptors composed mainly of O-terminal oligosaccharides. Fish eggs have a teleost equivalent of mammalian zona pellucida wherein the carbohydrate moiety has some structural similarity to the carbohydrate moiety of mammalian zona pellucida (Taguchi, T., Seko, A., Kitajima, K., Muko, Y., Inoue, S., Knoo, K-H., Morris, H. R., Dell, A. and Inoue, Y.(1994) "Structural studies of a novel type of pentaantennary large glycan unit in the fertilization-associated carbohydrate-rich glycopeptide isolated from the fertilized eggs of Oryzias latipes." J. Biol. Chem 269:8762–8771).

Mouse ZP2 (ZPA) contains a 241-amino acid domain at the C-terminus with 28% identity with a white flounder teleost egg protein (Lyons, C. E., Payette, K. L., Price, J. L. and Huang, R. C. C. (1993) "Expression and structural analysis of a teleost homolog of a mammalian zona pellucida gene." J. Biol. Chem. 268:21351–21358). A 348-amino acid sequence of mouse ZP1 (ZPB) is 47% similar (32% identical) to that of mouse ZP2 (ZPA) suggesting that this protein domain has been duplicated in mammals (Epifano, O., Liang, L-F. and Dean, J. (1996) "Mouse ZP1 encodes a zona pellucida protein homologous to egg envelope proteins in mammals and fish." J. Biol. Chem. 270: 27254–27258). A smaller region of this sequence (275 amino acids) is 52% similar (36% identical) with a white flounder egg envelope protein that contains 509 amino acids.

Immunization of grey seals with a single administration vaccine containing soluble zona pellucida antigens encapsulated in liposomes has been shown to reduce female fertility by at least 90% for up to at least six years (Brown, R. G., Kimmins, W. C., Mezei, M., Parsons, J. L., Pohajdak, B. and Bowen, W. D. (1996) "Birth control for grey seals." Nature 379:30–31; Brown, R. G., Bowen, W. D., Eddington, J. D., Kimmins, W. C., Mezei, M., Parsons, J. L., and Pohajdak, B. (1997) "Evidence for a long-lasting single administration contraceptive vaccine in wild grey seals." J. Reproduct. Immunol. 35:43–51; and U.S. Pat. No. 5,736, 141). The same vaccine prevented pregnancy in four rabbits (proven breeders) following 8 matings (unpublished observations).

An example of the use of liposome encapsulation of denatured recombinantly produced protein to raise antibodies against a native protein was shown with Neisseria meningitidis outer membrane protein P1. (Muttilainen, S., Idanpaan-Heikkila, I., Wahlstrom, E., Nurminen, M., Makela, P. H. and Sarvas, M. (1995) "The Neisseria meningitidis outer membrane protein P1 produced in Bacillus subtilis and reconstituted into phospholipid vesicles elicits antibodies to native P1 epitopes." Microb. Pathog. 18:423–436).

Specificity of recognition of sperm and egg is essential in any species. However, the mechanism of fertilization varies widely, both physiologically and biochemically, between species. Fertilization in fish differs from that in mammals in that most teleostean fish spermatozoa lack an acrosomal structure. Penetration by a spermatozoon of the fish egg envelope occurs via a discrete micropyle with closure of the micropyle after penetration of the first spermatozoon.

Sperm-egg interaction in birds is significantly different from that in mammals and different again from fish. In birds, sperm-egg recognition is initiated by the binding of spermatozoa to the inner perivitelline layer (IPVL), a proteinaceous structure surrounding the avian ovum (Bakst, M. R. and Howarth, B. (1977) "Hydrolysis of hens perivitelline layer by cock sperm in vitro." Biol. Reproduct. 17:370–379). There is no block to polyspermy in avian species but a further proteinaceous layer, the outer perivitelline layer (OPVL), is laid down about 15 minutes after the IPVL in chickens and appears to prevent further penetration of sperm. Therefore, if spermatozoa can be prevented from entering the avian egg between the laying down of the IPVL and OPVL, by antibodies directed against the IPVL, then immunocontraception would be realized.

There is some similarity between reproduction in mammals and fish but also many differences. Unlike the C-terminus, the N-terminus domain of white flounder egg protein is quite dissimilar to mouse ZP2 (ZPA) and a transmembrane domain characteristic of all mammalian zona pellucida proteins is not present in teleost egg protein indicating the divergence of these species 650 million years ago (Epifano, O., Liang, L-F. and Dean, J. (1996) "Mouse ZP1 encodes a zona pellucida protein homologous to egg envelope proteins in mammals and fish." J. Biol. Chem. 270: 27254–27258).

The carbohydrate moiety of teleost egg glycoproteins is also dissimilar, for example, rainbow trout egg envelope glycoprotein has a unique N-linked glycan containing KDN (2-keto-3-deoxy-D-glycero-D-qalacto-nononic acid) in the second layer of the vitelline envelope (Tezuka, T., Taguchi, T., Kanamori, A., Muto, Y., Kitajima, K., Inoue, Y. and Inoue, S. (1994) "Identification and structural determination of the KDN-containing N-linked glycan chains consisting of bi- and triantennary complex-type units of KDN-glycoprotein previously isolated from rainbow trout vitelline envelopes." Biochem. 33:6495–6502). This KDN-glycoprotein is exposed to the outer surface around the micropyle through which sperm enter the egg at fertilization. Most fish sperm lack an acrosome and penetrate the fish egg envelope via a discrete micropyle. The micropyle forms a guidance system in teleost fertilization that enhances sperm penetration (Amanze, D. and Iyengar, A. (1990) "The micropyle: a sperm guidance system in teleost fertilization."

Development 109:495–500). A chemical attractant may also emanate from the micropyle to enhance the chance of fertilization.

In spite of the significant structural differences between fish egg envelope protein and mammalian zona pellucida, fish egg envelope proteins have been designated the teleost homolog of zona pellucida (TH-ZP for convenience of reference). In fish, TH-ZP3 is made in the liver and transported via the blood to the ovary, while TH-ZP2 is made in the ovary (Hamazaki, T. S., Nagahama, Y. and Yamagami, K. (1989) "A glycoprotein from liver constitutes the inner layer of the egg envelope (zona pellucida interna) of the fish, *Oryzias latipes*." Dev.Biol.133:101–110; Murata, K., Sasaki, T., Yasumasu, S., Iuchi, I., Enami, J., Yasumasu, I. and Yamagami, K. (1995) "Cloning of cDNAs for the precursor protein of a low-molecular weight subunit of the inner layer of the egg envelope (chorion) of the fish *Oryzias latipes*."; Chang, Y. S., Wang, S. C., Tsao, C. C. and Huang, F. L. (1996) "Molecular cloning, structural analysis and expression of carp ZP3 gene." Mol. Reprod. Dev. 44:295–304; Murata, K., Sugiyama, H., Yasumasu, S., Iuchi, I., Yasumasu, I. and Yamagami, K. (1997) "Cloning of cDNA and estrogen-induced hepatic gene expression for chorigenin H, a precursor protein of the fish egg envelope (chorion)." Proc.Natl.Acad.Sci. USA 94:2050–2055; Chang, Y. S., Hsu, C. C., Wang, S. C., Tsao, C. C. and Huang, F. L. (1997) "Molecular cloning, structural analysis and expression of carp ZP2 gene." Mol. Reprod. Dev. 46:258–67).

It is undesirable that transgenic fish escape from fish farms and mate with fish in the wild. This problem would be reduced if females were sterile. Such sterile fish could also redirect their food reserves to increase their body size rather than roe production. Triploid fish are sterile but triploid salmon grow poorly (MacKenzie, D. (1996) "Can we make supersalmon safe?" New Scientist pp 14–15). Triploidy can be induced in fish by a pulse of pressure that prevents embryos from ejecting one set of chromosomes.

With respect to birds, population control of certain species is of great environmental importance. For example, some Canada geese (*Branta canadensis*) populations in the USA, Canada and Europe have increased to a point that threatens other bird populations and are a nuisance to the enjoyment of parks, golf courses, etc. Burgeoning populations of snow geese (*Chen caerulescens*) are wreaking havoc on precious tundra habitat (Struzik, E. (1998) "The snow geese dilemma." Equinox 97:50–57) and have resulted in compensation claims in Quebec, Canada alone of $844,000 in 1996. Some tundra habitats have been described as 35% overgrazed, 35% damaged and 30% destroyed by snow geese. In addition, many populations of small birds such as pigeons (*Columba livia*) and starlings (*Sturnus vulgaris*) cause significant economic loss in many parts of the world. As a consequence, there is need for management of some bird populations.

SUMMARY OF THE INVENTION

The present invention provides a single administration immunocontraceptive for fish.

More specifically, the present invention provides an immunocontraceptive vaccine composition comprising a teleost homolog of zona pellucida (TH-ZP), together with a pharmaceutically acceptable diluent or carrier, for preventing fertilization in a fish.

In another aspect, the present invention provides a method for preventing fertilization in a fish comprising administering an effective amount of the composition of the invention, comprising a teleost homolog of zona pellucida (TH-ZP), to the fish.

It is preferred that an adjuvant, such as Freund's complete adjuvant (FCA) or another biologically acceptable adjuvant, be present to assist in stimulation of an immune response in fish. It is also preferred that the TH-ZP be encapsulated into a liposome for administration. Preferably the liposome is multilamellar and comprises L-α-lecithin (soybean) and cholesterol, since this will effect slow release of TH-ZP resulting in an extended period of antibody production and thereby an extended period of contraception in fish. In addition, antibodies raised by this immunological procedure will be directed to the native protein antigens.

The present invention also provides a single administration immunocontraceptive for birds.

Accordingly, in another aspect, the present invention provides an immunocontraceptive vaccine composition comprising an antigen from an inner perivitelline layer (IPVL) of a bird egg, together with a pharmaceutically acceptable diluent or carrier, for reducing or preventing fertilization in a bird.

In another aspect, the present invention provides a method for preventing fertilization in a bird comprising administering an effective amount of the composition of the invention, comprising the antigen from an inner perivitelline layer (IPVL), to the bird.

It is preferred that an adjuvant, such as Freund's complete adjuvant (FCA) or another biologically acceptable adjuvant, be present to assist in stimulation of an immune response in birds.

It is preferred that the antigen from the IPVL, e.g. in an IPVL portion, be encapsulated into a liposome for administration. Preferably the liposome is multilamellar and comprises L-α-lecithin (soybean) and cholesterol, to effect slow release of antigen/IPVL and increase production of antibodies that bind to the target proteins. This will result in an extended period of antibody production and thereby an extended period of contraception in birds.

As well as FCA, other adjuvants that can be used in vaccine compositions of the present invention include non-ulcerative Freund's complete adjuvant, Freund's incomplete adjuvant, TITERMAX™, MF89, Gerbu, Bacillus Calmette-Guerin, RIBI (MPL+TDM+CWS), bacterial lipopolysaccharide, sodium phthalate derivative of bacterial lipopolysaccharide, sodium phthalate derivative of lipopolysaccharide plus alum, SUPERCARRIER™, ADJU-PRIME™ and Alum.

In general, any suitable liposome can be used in the fish or bird vaccine compositions disclosed herein. Anionic and neutral liposomes are well-known in the art (see, e.g., Liposomes: A Practical Approach, RPC New Ed, IRL press (1990), for a detailed description of methods for making liposomes) and are useful for delivering a large range of products.

Cationic lipids are also known in the art. Such lipids include Lipofectin™ also known as DOTMA (N-[1-(2,3-dioleyloxy)propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N', N'-dimethyl aminomethane)-carbamoyl) cholesterol). A description of these cationic lipids can be found in EP 187, 702, WO 90/11092, U.S. Pat. No. 5,283,185, WO 91/15501, WO 95/26356, and U.S. Pat. No. 5, 527, 928.

The route of administration of the vaccine compositions disclosed herein can be any route used typically used in the vaccine field. As general guidance, administration can be via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends on the formulation that is selected as well as on the animal to be vaccinated.

Administration is achieved in a single dose or repeated as necessary at intervals, as can be determined readily by one skilled in the art. An appropriate dose depends on various parameters including the recipient (e.g., adult or infant), the particular vaccine antigen, the route and frequency of administration and the presence/absence or type of adjuvant as can be determined by one skilled in the art.

It should be noted that all of the antibody titers referred to in the specification are measured in comparison with the antibody titer in a reference serum. The titer in the reference serum was arbitrarily assigned a value of 100. That value has no relationship to the absolute titer required to produce an immunocontraceptive effect. In fact, titers of only a few percent of those found in the reference serum are sufficient to produce an immunocontraceptive effect in some cases. While the reference serum clearly contains sufficient antibody to effect immunocontraception, it does not represent an indication of the minimum antibody titer needed for immunocontraception.

DETAILED DESCRIPTION OF THE ION

1. Fish

Preferred methods of purifying TH-ZP from the eggs of exemplified fish species are set out below. Rabbits were conveniently used for production of anti-TH-ZP sera for screening fractions obtained during purification of TH-ZP. Any species of fish can be immunized provided the TH-ZP used in the vaccine is different enough from the targeted fish species to provoke a good immune response but similar enough that the antibodies produced cross-react with the targeted species TH-ZP. In practice, species that are farmed commercially, including transgenic fish such as salmon, rainbow trout and tilapia, would be important targets.

Collection of Fish Eggs.

Atlantic salmon (*Salmo salar*), American plaice (*Hippoglossoides platessoides*), herring (*Clupea harengus*) and haddock (*Melanogrammus aeglefinus*) eggs were obtained from local commercial suppliers. Tilapia eggs were obtained from a colony of hybrid tilapia (*Oreochronis mossazmbicus X hornorum*) maintained in the Aquatron, Dalhousie University. Medaka eggs were harvested daily from a colony of Indian medaka (*Oryzias latipes*) and stored at −20° C. until extracted. Perch (*Perca flavescens*) and smelt (*Osmerus mordax*) eggs were obtained from fish caught in Lake Simcoe, Ontario and stored at −20° C. until extracted.

Extraction of TH-ZP.

The method used to extract the teleost homolog of zona pellucida (TH-ZP) depended on the quantity of eggs available. Method 1 was used when the wet weight of eggs was under 100 g. Method 2 was used when the wet weight of eggs was over 100 g.

Extraction Method 1.

Fish eggs were placed in a Wheaton tissue homogenizer (30 ml) equipped with a Teflon plunger. The plunger was pushed to the bottom of the tube and up to the top until microscopical examination indicated that most eggs were broken. The egg ghosts were collected on a nylon screen (48 μm pore size) and washed with cold saline to remove cytoplasm. Egg ghosts were replaced in the tissue homogenizer and agitated with the plunger to wash any remaining cytoplasm out of the ghosts. Microscopical examination was used to judge when the egg ghosts were free of cytoplasm. The egg ghosts were suspended in Tris buffer (20 mM, pH 8.0) and incubated at 75° C. in a water bath for 25 minutes. The suspension was vortexed and centrifuged (16,000×g for 15 minutes). The supernatant fluid was dialyzed, freeze dried and stored at −20° C.

Extraction Method 2.

Fish eggs were suspended in saline and the suspension placed in a Waring blender. The suspension was blended for 30 seconds and the egg ghosts collected on a nylon screen (pore size 500 μm). The ghosts were washed with liberal amounts of cold saline. The egg ghosts were resuspended in saline and replaced in the Waring blender for 30 seconds. The egg ghosts were collected on a nylon screen (pore size 209 μm) and washed with cold saline. The egg ghosts were extracted with Tris buffer as described in method 1.

Detection of TH-ZP.

Proteins in fish egg extracts were labelled with $^{14}C$ by reductive methylation (Jentoft, N. and Dearborn, D. G. (1979) "Labelling of proteins by reductive methylation using sodium cyanoborohydride." J.Biol.Chem. 254:4359–4365) so that fractions obtained during purification procedures could be monitored by determination of radioactivity. Crude extracts (10 mg) were dissolved in Hepes buffer (20 ml, pH 7.5, 0.1 M) to which $^{14}C$-formaldehyde (10 μCi, 37 mCi/mmol) was added. NaCNBH$_4$ was added in two equal portions, one at the beginning and one following 30 minutes incubation at 20° C., to give a final concentration of 20 mM. After 60 minutes incubation, the reaction mixture was acidified with acetic acid and dialyzed overnight. The labelled product was recovered by freeze drying.

To produce TH-ZP that was not radioactive, purification procedures were repeated with unlabelled egg extracts. In this case, fractions were monitored for protein with bicinchoninic acid (Sigma) using bovine serum albumin as a reference standard.

Fractions were also monitored by ELISA using rabbit anti-haddock TH-ZP serum during purification of herring, smelt and perch TH-ZP. Aliquots of fractions from gel chromatography, ion exchange chromatography and isoelectric focussing were diluted to contain protein in the range 10–100 μg/ml with sodium carbonate/bicarbonate buffer (Na$_2$CO$_3$ 0.015 M; NaHCO$_3$, 0.035 M; pH 9.6). The diluted fractions (100 µL) were placed in wells of a microtiter plate and proteins allowed to absorb at 37° C. for 1 hour. Material not absorbed was removed and the wells coated with gelatin (3% in TBST buffer—Tris, 0.01 M; NaCl, 0.15 M; 0.05% Tween 20; pH 8.0) for 10 minutes followed by washing 5×'s with TBST buffer. Rabbit anti-haddock TH-ZP serum (100 µL, diluted 1:100 with TBST buffer) was added to each well and the microtiter plate incubated at 37° C. for 1 hour. Unbound antibody and other serum proteins were removed by washing with TBST buffer (5×'s). Bound antibody was measured with protein A/alkaline phosphatase using a Dynatech ELISA plate reader at 405 nm.

Chromatography.

Gel chromatography used TSK-gel (toyopearl HW-65F, 1.5×58 cm) eluted with Tris buffer (0.01 M, pH 7.5 containing 0.01% NaN) at a flow rate of 15 ml/hr. Crude TH-ZP extracts were dissolved in Tris buffer (0.01 M, pH 7.5, 5 ml), centrifuged to remove any insoluble material and aliquots (2 ml) used for gel chromatography. Fractions (3 ml) were collected and aliquots from each fraction were analyzed for radioactivity, protein or ELISA using rabbit anti-haddock TH-ZP serum.

Ion exchange chromatography used Sephacel DEAE (1.5×22 cm) eluted with Tris buffer (0.01 M, pH 8) having a linear gradient from 0 to 0.3 M. NaCl in a total volume of 150 ml at a flow rate of 6.4 ml/hr. Fractions were collected (3.1 or 6.2 ml) and aliquots of each fraction were analyzed for radioactivity, protein or by ELISA using rabbit anti-haddock TH-ZP serum.

Isoelectric Focussing.

Preparative isoelectric focussing used a Rotofor (Biorad) at a constant power input of 12 W for 4 hr. The RotoLytes (Biorad) used were in the range pH 3–9 formed from combining RotoLytes in the range 2.9–4.1;4.5–6.1;6.4–7.5 and 7.8–8.9. Twenty fractions were collected and the pH of each fraction was adjusted to pH 7–8 with acetic acid or solid NaHCO$_3$. Aliquots of each fraction were analyzed for TH-ZP by determination of radioactivity or ELISA using rabbit anti-haddock TH-ZP or rabbit anti-herring TH-ZP sera.

SDS-PAGE.

SDS-PAGE used gradient gels (Biorad) and kaleidoscope standards to determine molecular weights. Gels were stained with coomassie blue or used for Western blotting with rabbit anti-haddock TH-ZP.

Rabbit Anti-TH-ZP Sera.

Rabbit anti-TH-ZP sera were produced by immunizing one rabbit for each TH-ZP type with a preparation of haddock TH-ZP that produced a single band (44 kDa) following SDS-PAGE and coomassie blue staining or a preparation of herring TH-ZP obtained by gel chromatography and isoelectric focussing that Western blotting indicated contained a single band (44 kDa).

Immunization of Rainbow Trout.

Three rainbow trout for each TH-ZP preparation were immunized by a single intramuscular injection (18 gauge, 2.5 in. needle) with TH-ZP (50 µg) encapsulated in liposomes containing phospholipon 90G (Nattermann Phospholipid, Cologne, Germany, 0.04 g) and cholesterol (0.004 g) in saline (0.3 ml). A single dose of the vaccine contained liposomes (0.3 ml, 50 µg TH-ZP) emulsified in Freund's complete adjuvant (FCA, 0.3 ml). Mean body masses of rainbow trout at the time of vaccination were in the range 1.4–1.8 kg. Six rainbow trout were not immunized and served as controls.

Determination of Rainbow Trout Anti-TH-ZP Antibody Titers.

Rainbow trout were anesthetized with MS 222 and blood samples taken from the caudal vein before immunization and 1, 3, 5, 6 and 8 months post-immunization.

Anti-TH-ZP antibody titers were measured by ELISA using a 96-well microtiter plate. To each well, TH-ZP (1 µg) in sodium carbonate/bicarbonate buffer (100 µL) was allowed to adsorb at 37° C. for 1 hour. TH-ZP not adsorbed was removed. Plates were coated with gelatin as previously described. Rainbow trout serum samples were added in doubling dilutions using TBST from 1/25 to 1/3200 and incubated at 20° C. for 1.5 hours. Unbound antibody and other serum proteins were removed by washing with TBST (5×'s). Mouse monoclonal IgM anti-chinook salmon antibody (100 µL, 1/100 dilution in TBST) was added to all wells. Although the mouse MAb was raised against chinook salmon antibody, the mouse MAb bound strongly to rainbow trout antibody reflecting the close phylogenetic relationship between the two salmonid species. The plate was incubated for 1.5 hours at 20° C. Unbound antibody was removed by washing with TBST (5×'s). Bound mouse monoclonal antibody was measured with goat anti-mouse IgM-alkaline phosphatase solution (100 µL, diluted 1:1000 with TBST from liquid stock, Sigma) using a Dynatech ELISA plate reader at 405 nm. One row in each plate did not receive serum (antibody) and served as a blank. Another row in each plate received doubling dilutions of a reference serum. The reference serum was anti-medaka TH-ZP serum that has a titer of 6,400. Production of antibodies by rainbow trout is expressed relative to this serum to avoid interassay variability.

Ova Production.

Rainbow trout normally spawn in the spring, however, the rainbow trout used in this study were from St. Peter's fish hatchery, Nova Scotia, Canada and spawn in the autumn (Herbinger, C. M., Doyle, R. W., Pitman, E. R., Paquet, D., Mesa, K. A., Morris, D. B., Wright, J. M. and Cook, D. (1995) "DNA fingerprint based analysis of paternal and maternal effects on offspring growth and survival in communally reared rainbow trout. Aquaculture 137:245–256). To measure ova production, treated and control rainbow trout (three fish in each treatment group were weighed then the ova were removed and weighed. Rainbow trout immunized with smelt TH-ZP, herring TH-ZP and perch TH-ZP and three control fish were processed on November 7 (six months post-immunization). Since the ova weighed less than expected, the remaining rainbow trout were maintained for another month (eight months post-immunization) before being processed.

Extraction of TH-ZP.

Extraction of haddock roe (1.1 kg wet weight) yielded a crude preparation of haddock TH-ZP that weighed 949 mg and extraction of herring roe (230 g wet weight) yielded a crude preparation of herring TH-ZP that weighed 152 mg. Yields of crude TH-ZP preparations from other fish roe were similar.

Reductive Methylation of TH-ZP.

Reductive methylation of crude preparations of TH-ZP On yielded material having. radioactivity in the range 545–9770 DPM/mg protein.

Purification of TH-ZP.

Figure 1:
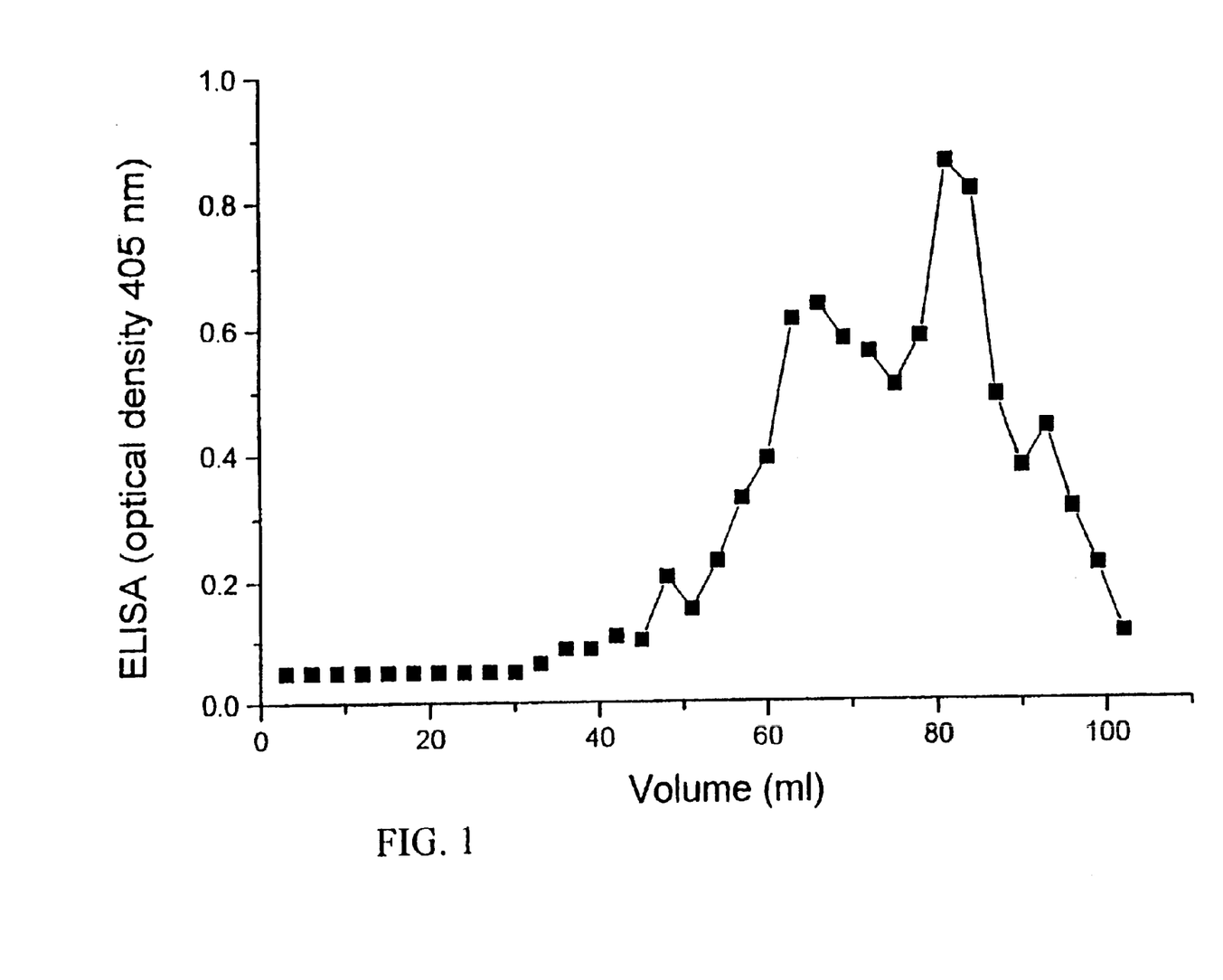
FIG. 1 shows a gel chromatography profile of herring TH-ZP. Fractions 60–75 and 78–80 ml were pooled, dialyzed and freeze-dried.

Gel chromatography of most crude extracts of TH-ZP yielded one broad peak as detected by ELISA using rabbit anti-haddock TH-ZP serum or by measurement of protein or radioactivity. Fractions containing the major peak were pooled, dialyzed and freeze dried. Based on recovery of protein or radioactivity, yields were lower than expected (for example, 20 mg of 61 mg placed on the gel) suggesting that gel chromatography removed non-protein components, but did little to resolve proteins. In some cases, two peaks were obtained (FIG. 1). In these cases, each peak was pooled, dialyzed, and freeze dried.

Figure 2:
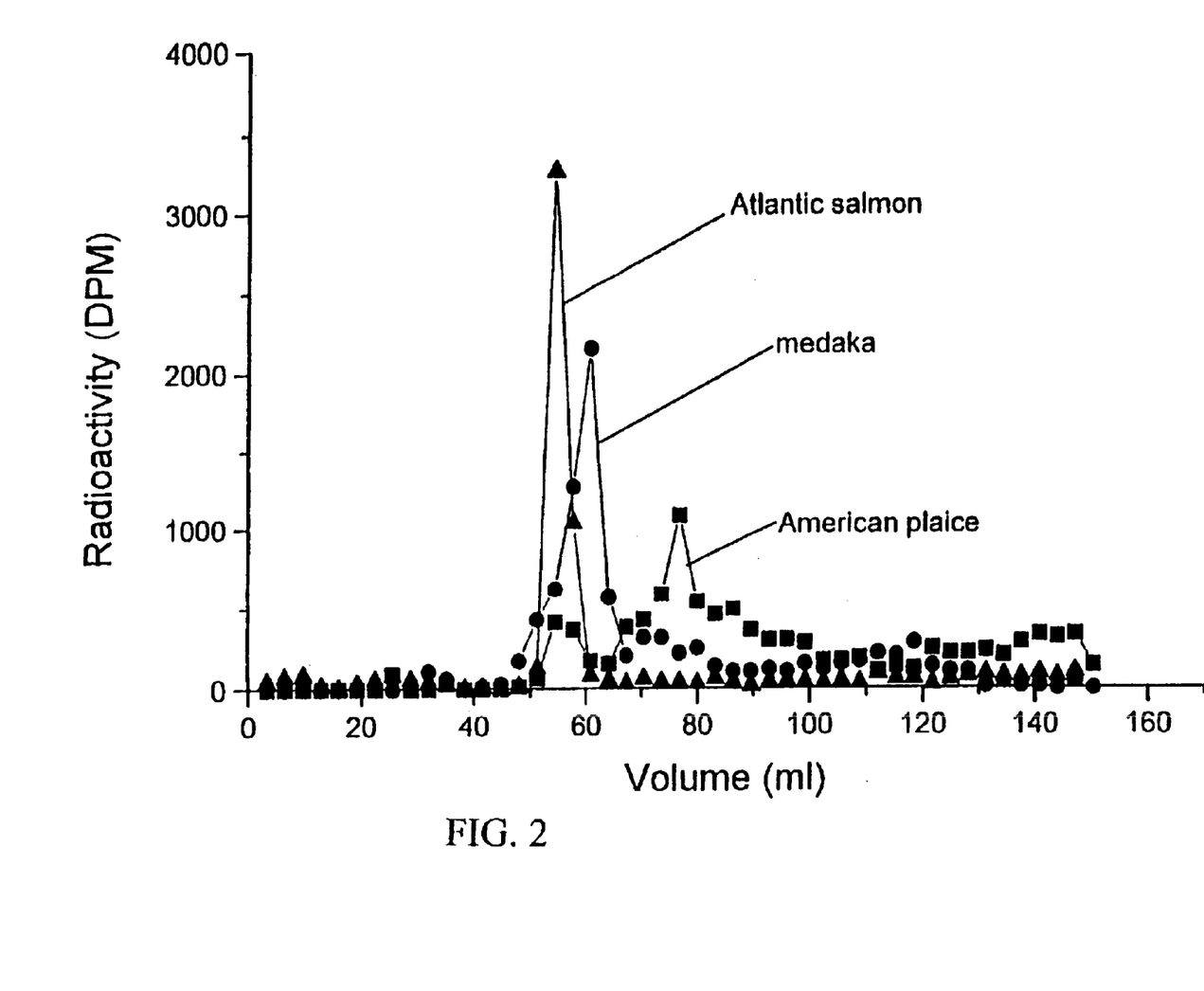
FIG. 2 shows an ion exchange chromatography profile of American plaice, Atlantic salmon and medaka TH-ZP. Each major peak (64–83 ml, American plaice; 54–70 ml Atlantic salmon; 54–64 ml medaka) was pooled, dialyzed and freeze dried.

The freeze dried material was chromatographed on Sephacel-DEAE (FIG. 2). Fractions were analysed by ELISA or for radioactivity, pooled, dialyzed and freeze dried. SDS-PAGE was used to assess purity of preparations. American plaice, haddock, medaka and tilapia TH-ZP preparations contained a single protein band (44 kDa) and were not further purified. The expected molecular weight was 45 kDa based on a polypeptide chain of 509 amino acids (Lyons et al., 1993). The Atlantic salmon TH-ZP preparation contained a major band at 90 kDa and minor bands at 29 and 87 kDa.

Figure 3:
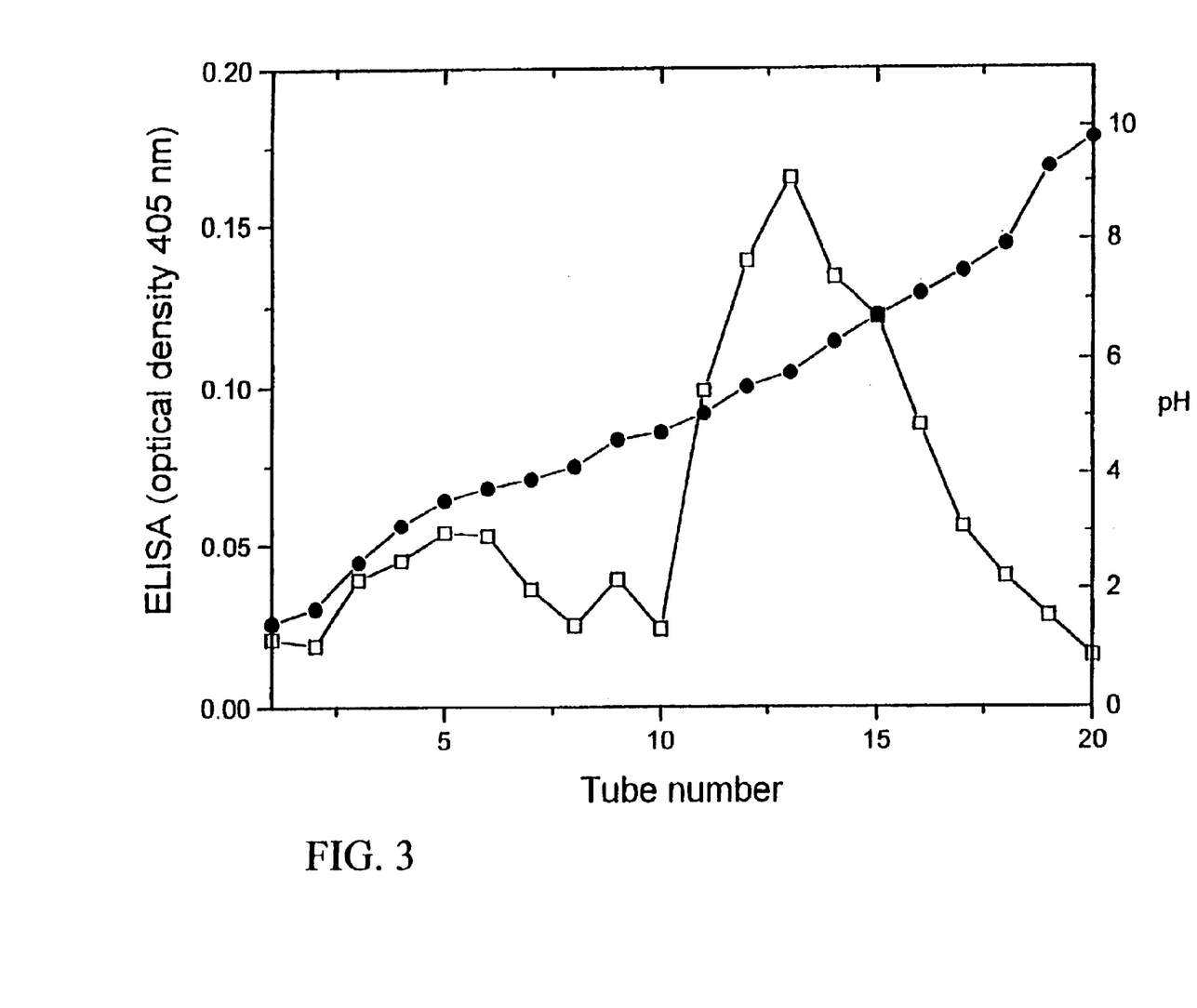
FIG. 3 shows the results of an isoelectric focussing purification of herring TH-ZP. Tubes 12–15 (inclusive) were pooled, dialyzed and freeze dried.

Herring, smelt and perch TH-ZP preparations were further purified by preparative isoelectric focussing (FIG. 3). Following isoelectric focussing, coomassie blue staining of a SDS-PAGE gel detected a wide band (40–120 kDa) in the herring, perch and smelt TH-ZP preparations. A Western blot using rabbit anti-haddock TH-ZP serum detected only one band (44 kDa) in the herring preparation suggesting coomassie blue staining material on either side of the major band was present in minor quantities and was unrelated to TH-ZP. Western blotting of SDS-PAGE gels detected two bands in the smelt preparation (70 and 90 kDa) and two major bands in the perch preparation (29 and 70 kDa). Although the preparations of Atlantic salmon TH-ZP, smelt TH-ZP and perch TH-ZP contained more than one protein and the molecular weights of these proteins differed from the expected value of 45 kDa, detection by rabbit anti-haddock TH-ZP serum in Western blots suggests that the material in the Atlantic salmon, perch and smelt preparations was related to TH-ZP. Therefore, these preparations as well as the other TH-ZP preparations were used to immunize rainbow trout.

Production of Anti-TH-ZP Antibodies by Rainbow Trout.

Figure 4:
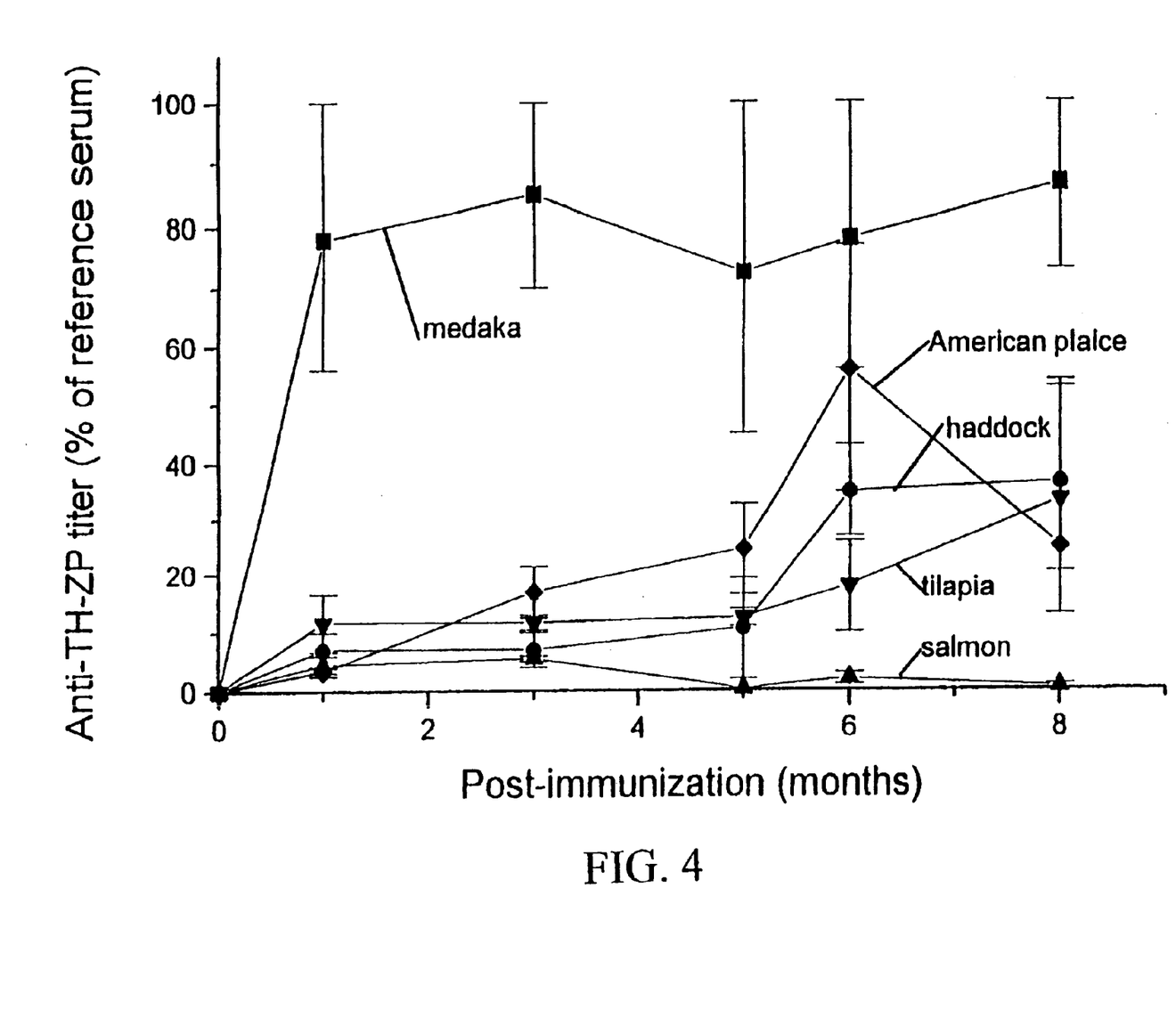
FIG. 4 shows the production of anti-TH-ZP antibodies by rainbow trout immunized with Atlantic salmon TH-ZP, American plaice TH-ZP, tilapia TH-ZP, medaka TH-ZP and haddock TH-ZP.

Rainbow trout immunized with medaka TH-ZP produced the most antibody (FIG. 4). Production of anti-TH-ZP antibodies by rainbow trout immunized with TH-ZP from American plaice, haddock, and tilapia was similar. Antibody titers increased during the 8 months post-immunization period but the increase was not linear; titers were highest 6 or 8 months post-immunization. Titers of sera from rainbow trout immunized Atlantic salmon TH-ZP were low. Anti-Atlantic salmon TH-ZP titers were highest 3 months post-immunization but declined thereafter. Measurement of crossreactivity using rainbow trout anti-sera collected six months post-immunization confirmed the low anti-Atlantic salmon TH-ZP titers and indicated that rainbow trout produced the highest titer when immunized with medaka TH-ZP (TABLE 1). Crossreactivity generally reflected phylogenetic relationship among the fish species investigated, that is, anti-TH-ZP sera crossreact strongest with TH-ZP from fish that are phylogenetically related. This relationship was not true of sera from trout immunized with TH-ZP from smelt, herring and perch (TABLE 2) These sera were obtained from rainbow trout early in roe production when TH-ZP 3 is being transported from the liver to the ovary via the blood. If contact between antibodies and TH-ZP 3 is high, this could result in removal of anti-TH-ZP antibodies binding to rainbow trout TH-ZP 3. This proposal is supported by the observation that rainbow trout anti-herring TH-ZP antibodies bound best to herring and perch TH-ZP, the two TH-ZP types least related phylogenetically to rainbow trout TH-ZP (TABLE 3). In contrast, rainbow trout anti-haddock TH-ZP serum crossreacted with TH-ZP from teleosts in the order predicted by phylogenetic relationships. One possible explanation is that when rainbow trout anti-haddock TH-ZP serum was being collected, the terminal stage in roe production was reached and less TH-ZP 3 was present in blood to remove anti-TH-ZP antibodies crossreacting with rainbow trout TH-ZP. As a consequence, anti-TH-ZP antibodies recognizing medaka, tilapia, American plaice and Atlantic salmon TH-ZP were able to accumulate in the blood.

Rabbit anti-haddock TH-ZP and anti-herring TH-ZP sera crossreacted best with TH-ZP from fish closest phylogenetically to either haddock TH-ZP or herring TH-ZP. Rainbow trout anti-haddock TH-ZP serum demonstrated a similar relationship suggesting that rainbow trout can make antibodies with the same discriminating specificity as mammals. Perch TH-ZP was the exception. Rabbit anti-haddock TH-ZP and rabbit anti-herring TH-ZP sera recognized perch TH-ZP better than would be predicted from phylogenetic considerations. Interestingly, rainbow trout anti-herring TH-ZP serum also recognized perch TH-ZP better than expected based on phylogeny.

Ova Production.

When ova production was measured, many of the rainbow trout were found to be males. This was unexpected since presumably this study started with all female rainbow trout. As a consequence, sample sizes are not large enough to permit statistical analysis (TABLE 4).

In spite of the above problem, the results suggest that immunization of rainbow trout with salmon TH-ZP, haddock TH-ZP, herring TH-ZP or perch TH-ZP reduces roe production.

American plaice, haddock, medaka, tilapia and herring TH-ZP preparations contained a single protein having the expected molecular weight of 45 kDa. Atlantic salmon, smelt and perch TH-ZP preparations contained more than one protein with molecular weights that differed than the expected value of 45 kDa. Western blots suggested that these proteins were related to TH-ZP from other teleosts and therefore these proteins were included in the present study.

Of the TH-ZP preparations studied, immunization of rainbow trout with salmon, haddock, herring or perch TH-ZP reduced roe production. The difficulty of determining the sex of experimental animals caused too few females to be included in each experimental group, consequently, statistical analysis of the results was not possible.

Relating anti-TH-ZP antibody titers and crossreactivity to roe production was difficult as the quantity of roe produced is a significant portion of fish weight. Consequently, significant quantities of antibodies could be bound to TH-ZP 3 as TH-ZP 3 was being transported from the liver to the ovary and consequently would not be available during measurements of titers and determination of crossreactivity. This potential difficulty would be greatest when roe production was maximal.

TABLE 1

Anti-TH-ZP titers in rainbow trout six months postimmunization.

| Vaccine TH-ZP | Titer (% of reference serum)[1] TH-ZP used in ELISA assay | | | | |
|---|---|---|---|---|---|
| | Tilapia | Atlantic salmon | Haddock | American plaice | Medaka |
| Tilapia | 33 | 5 | 19 | 11 | 44 |
| Atlantic salmon | 8 | 3 | 3 | 2 | 18 |
| Haddock | 19 | 2 | 67 | 9 | 52 |
| American plaice | 11 | 6 | 7 | 85 | 26 |
| Medaka | 23 | 8 | 16 | 7 | 100 |

[1]Each titer is an average of measurements using sera from three rainbow trout immunized with the same antigen. The average titer of sera from rainbow trout immunized against medaka TH-ZP was arbitrarily set at 100.

TABLE 2

Anti-TH-ZP titers in rainbow trout three months postimmunization.

| Vaccine TH-ZP | Titer (% of reference serum)[1] TH-ZP used in ELISA assay | | |
|---|---|---|---|
| | smelt | herring | perch |
| smelt | 3 | 1 | 0 |
| herring | 8 | 58 | 30 |
| perch | 5 | 14 | 65 |

[1]Titer is expressed relative to a rainbow trout anti-medaka TH-ZP sera to avoid interassay variability.

TABLE 3

Crossreactivity of rainbow trout anti-herring and anti-haddock TH-ZP and rabbit anti-herring and anti-haddock TH-ZP sera.

| TH-ZP used in ELISA | Titer (% of homologous serum)[1] | | | |
|---|---|---|---|---|
| | anti-herring TH-ZP | | anti-haddock TH-ZP | |
| | rainbow trout | rabbit | rainbow trout | rabbit |
| herring | 100 | 100 | ND | 81 |
| haddock | 2 | 45 | 100 | 100 |
| medaka | 4 | 3 | 77 | 7 |
| tilapia | 1 | 0 | 28 | 4 |
| American plaice | 1 | 0 | 13 | 2 |
| Atlantic salmon | 0 | 41 | 3 | 12 |
| smelt | 2 | 11 | ND | 140 |
| perch | 43 | 93 | ND | 68 |

[1]Titers of anti-TH-ZP sera are expressed as a percentage of the homologous anti-serum. ND = not determined.

TABLE 4

Effect of immunization of rainbow trout with TH-ZP on ova production.

| Trial 1 | | Trial 2 | |
|---|---|---|---|
| vaccine Ag | ova production (% of fresh weight) | vaccine Ag | ova production (% of fresh weight) |
| Control | 1.87 | Control | 14.2 |
| | 1.63 | | |
| | | Atlantic salmon | 6.7 |
| smelt | 1.54 | | 9.3 |
| herring | 0.93 | haddock | 6.7 |
| | 1.28 | | 10.5 |
| perch | 0.98 | American plaice | 11.7 |
| | | medaka | 12.2 |
| | | | 8.8 |
| | | tilapia | 14.7 |
| | | | 10.8 |
| | | | 14.1 |

2. Birds

Preferred methods of purifying the inner perivitelline layer (IPVL) from eggs of exemplified bird species are set out below. Any bird species can be immunized provided the correct balance between foreignness of IPVL to provoke a good immune response and relatedness to foster good cross-reactivity is chosen. This requires matching the target species with the bird species from which the IPVL is obtained and used as antigen in the vaccine. In practice, a bird species in need of population control such as the Canada goose (*Branta canadensis*) would be chosen.

Antigen.

The inner perivitelline layer (IPVL) of chicken, duck and goose eggs was isolated from laid eggs as described by Robertson, L., Brown, H. L., Staines, H. J. and Wishart, G. J. (1997) "Characterization and application of an avian in vitro spermatozoa-egg interaction assay using the inner perivitelline layer from laid chicken eggs." J. Reproduct. Fertil. 110:205–211. Goose or duck IPVL (0. 2 mg/ml) was suspended in Tris (pH 9.0, 0.01 M) buffered saline at 25° C. for 30 minutes. The resulting suspension was encapsulated in liposomes as described below.

Vaccine.

A single dose of the vaccine contained either goose or duck IPVL (50 $\mu$g) suspended in Tris buffered saline (250 $\mu$L). Duck or goose IPVL was encapsulated in multilamellar liposomes and suspended in Freund's complete adjuvant (FCA; 0.25 ml) as previously described (Brown et al., 1997). The placebo vaccine contained all the above except IPVL. Brown Leghorn chickens (1.3–1.9 kg; 54 weeks old) were immunized by injection into the breast (22 gauge, 1.5 in. needle).

Titers.

Blood samples were taken from the wing vein and allowed to clot. Sera were recovered from the blood samples by centrifugation. Anti-goose IPVL and anti-duck IPVL titers were measured by ELISA using affinity purified rabbit anti-chicken IgG (Sigma C-2288) and protein A/alkaline phosphatase. All anti-goose IPVL and anti-duck IPVL titers are expressed relative to the titer of the 1.5 month post-immunization anti-sera of chickens 1179 and 1049, respectively.

Egg Fertility.

All hens were artificially inseminated twice, three days apart, with pooled semen from nine Barred Rock roosters immediately following semen collection. Beginning one day after the second insemination, eggs were collected daily over a 14 day period and stored at 7° C. until incubation. All eggs were incubated at 37.5° C., 60% relative humidity and turned three times daily until hatching. The eggs were candled at days 7 and 14, and infertile eggs evaluated by breakout. Fertile eggs were incubated until hatching to assess the effect of vaccination on chick development.

Results and Discussion.

Immunization of chickens with goose and duck IPVL produced antibodies that persisted during the period when eggs were collected from immunized hens (Table 5). The fertility of eggs from chickens that received the placebo vaccine was high (Table 6). A slight reduction in fertility occurred during development of the chicken embryo from fertilization until hatching. The fertility of eggs from chickens that were immunized with goose IPVL also showed a slight reduction in fertility during incubation (Table 7). There was no significant difference in fertility between eggs from chickens that received the placebo vaccine and eggs from chickens that were immunized with goose IPVL following 14 days incubation ($X^2=0.203$; $P=0.6$). The fertility of eggs from chickens that were immunized with duck IPVL was significantly less than the fertility of eggs from chickens that received the placebo vaccine (Table 8; $X^2=4.63$; $P=<0.005$). These results demonstrate that immunization of chickens with duck IPVL can significantly reduce the fertility of chicken eggs.

Immunization of chickens with goose IPVL and duck IPVL did not significantly affect fertility after the eggs were laid based on analysis of the decline in fertility from day 0 to day 14 among fertile eggs ($x^2=0.871$; 2 df; $P=>0.5$). Therefore, the differences in fertility between treatments are due to causes arising before laying.

The percent of chicken anti-goose IPVL and anti-duck IPVL antibodies that bound to chicken IPVL varied from 1.6–7.3% for anti-goose IPVL and 0–5.2% for anti-duck IPVL (Table 9). Therefore, the quantity of anti-goose IPVL and anti-duck IPVL antibody binding to chicken IPVL is low.

PAGE of IPVL from chicken, goose and duck eggs followed by Western analysis using chicken anti-goose IPVL identified proteins having molecular weights of 48,000 and 45,000 as the main antigens in chicken IPVL. Selection of IPVL from bird eggs that crossreacted more strongly with chicken IPVL would improve the reduction in fertility.

It is expected that goose IPVL and duck IPVL will be similar to IPVL from snow and Canada geese, which are one possible target species. Therefore, effectiveness in fertility reduction when this vaccine is administered to snow and Canada geese is expected.

TABLE 5

Production of anti-goose IPVL and anti-duck IPVL antibodies by chickens immunized against goose IPVL and duck IPVL using liposome delivery.

| Chicken ID | Anti-IPVL titres Treatment[1] | (% of reference serum) Post-immunization (days) | | |
|---|---|---|---|---|
| | | 0 | 45 | 72 |
| 1009 | Placebo | 0 | 0 | 0 |
| 946 | | 0 | 0 | 0 |
| 1080 | | 0 | 0 | 0 |
| 1075 | | 0 | 0 | 0 |
| 1055 | | 0 | 0 | 0 |
| 1030 | | 0 | 0 | 0 |

TABLE 5-continued

Production of anti-goose IPVL and anti-duck IPVL antibodies by chickens immunized against goose IPVL and duck IPVL using liposome delivery.

| Chicken ID | Anti-IPVL titres Treatment[1] | (% of reference serum) Post-immunization (days) | | |
|---|---|---|---|---|
| | | 0 | 45 | 72 |
| 1179 | Goose IPVL | 0 | 100 | 62 |
| 1012 | | 0 | 89 | 57 |
| 694 | | 0 | 81 | 44 |
| 1081 | | 0 | 74 | — |
| 639 | | 0 | 89 | 82 |
| 690 | | 0 | 98 | 80 |
| 1019 | | 0 | 92 | 79 |
| 1074 | | 0 | 79 | 70 |
| 1049 | Duck IPVL | 0 | 100 | 76 |
| 1093 | | 0 | 98 | 83 |
| 1031 | | 0 | 67 | 43 |
| 650 | | 0 | 97 | 98 |
| 695 | | 0 | 81 | 80 |
| 1032 | | 0 | 53 | 76 |
| 1026 | | 0 | 39 | 39 |
| 637 | | 0 | 25 | 14 |

[1]Reference sera were from chickens 1179 and 1049 at one and one-half months post-immunization for goose and duck IPVL respectively.

TABLE 6

Fertility of eggs from chickens immunized with a placebo vaccine.

| Chicken ID | Post-immunization[1] (days) | Fertility status post-laying (days) | | | | |
|---|---|---|---|---|---|---|
| | | 0 | 1 | 7 | 14 | hatch |
| 1009 | 58 | F | F | F | F | F |
| | 60 | F | F | F | F | F |
| | 62 | F | F | F | F | F |
| | 63 | F | F | F | F | F |
| | 65 | F | I | I | I | I |
| | 68 | F | F | F | F | F |
| | 69 | F | F | F | F | F |
| 946 | 56 | F | F | F | F | F |
| | 59 | F | F | F | F | F |
| | 61 | F | F | F | F | F |
| | 62 | F | F | F | F | F |
| | 63 | F | F | F | F | F |
| | 64 | F | F | F | F | F |
| | 66 | F | F | F | F | F |
| | 68 | F | F | F | F | F |
| | 70 | F | F | F | F | F |
| | 72 | F | F | F | F | F |
| 1080 | 56 | F | F | F | F | F |
| | 57 | F | F | F | F | F |
| | 59 | F | F | F | F | F |
| | 61 | I | I | I | I | I |
| | 62 | F | F | F | F | F |
| | 63 | F | F | F | F | F |
| | 64 | F | F | F | F | F |
| | 66 | F | F | F | F | F |
| | 69 | F | F | F | F | F |
| | 70 | F | F | F | F | F |
| | 72 | F | F | F | F | — |
| 1075 | 57 | F | I | I | I | I |
| | 58 | F | F | F | F | F |
| | 59 | F | I | I | I | I |
| | 61 | F | F | F | F | — |
| | 62 | F | I | I | I | I |
| | 63 | F | F | F | I | I |
| | 66 | F | I | I | I | I |
| | 67 | F | F | F | F | F |

TABLE 6-continued

Fertility of eggs from chickens immunized with a placebo vaccine.

| Chicken ID | Post-immunization[1] (days) | Fertility status post-laying (days) | | | | |
|---|---|---|---|---|---|---|
| | | 0 | 1 | 7 | 14 | hatch |
| | 69 | F | F | F | F | F |
| | 70 | F | F | F | F | — |
| | 72 | F | F | F | F | — |
| 1056 | 57 | F | F | F | F | F |
| | 58 | F | F | F | F | F |
| | 59 | F | F | F | F | F |
| | 60 | F | F | F | F | F |
| | 62 | F | F | F | F | F |
| | 63 | F | F | F | F | F |
| | 64 | F | F | F | F | F |
| | 66 | F | F | F | F | F |
| | 67 | F | F | F | F | F |
| | 70 | F | F | F | F | F |
| | 72 | F | F | F | F | F |
| Percent fertile | | 98 | 88 | 88 | 86 | 82 |

[1]Time post-immunization that the egg was laid.
F = fertile; I = infertile; — = not determined

TABLE 7

Fertility of eggs from chickens immunized with goose IPVL.

| Chicken ID | Post-immunization[1] (days) | Fertility status post-laying (days) | | | | |
|---|---|---|---|---|---|---|
| | | 0 | 1 | 7 | 14 | hatch |
| 1179 | 57 | F | F | F | F | F |
| | 59 | F | F | F | F | F |
| | 60 | F | I | I | I | I |
| | 62 | F | I | I | I | I |
| | 63 | F | F | F | F | I |
| | 65 | F | F | F | F | F |
| | 68 | F | F | F | F | F |
| | 70 | F | F | F | F | F |
| | 72 | F | F | F | F | F |
| 1012 | 56 | F | F | F | F | F |
| | 57 | F | F | F | F | F |
| | 59 | F | F | F | I | I |
| | 60 | F | F | F | F | F |
| | 62 | F | F | F | F | F |
| | 63 | I | I | I | I | I |
| | 65 | F | F | F | F | F |
| | 66 | F | F | F | F | F |
| | 68 | F | F | F | F | F |
| | 69 | F | I | I | I | I |
| | 70 | F | F | F | F | F |
| 694 | 57 | I | I | I | I | I |
| | 58 | F | F | F | F | F |
| | 59 | F | F | I | I | I |
| | 61 | F | F | F | F | F |
| | 62 | F | F | F | F | F |
| | 63 | F | F | F | F | F |
| | 65 | F | F | F | F | F |
| | 66 | F | F | F | F | F |
| | 68 | F | F | F | F | F |
| | 69 | F | F | F | F | F |
| | 70 | F | F | F | F | F |
| 690 | 56 | F | F | F | F | F |
| | 58 | F | F | F | F | F |
| | 59 | F | F | F | F | F |
| | 61 | F | I | I | I | I |
| | 62 | F | F | F | F | F |
| | 63 | F | F | F | F | F |
| | 65 | F | F | F | I | I |
| | 66 | F | F | F | F | F |
| | 68 | F | F | F | F | F |
| | 72 | F | F | F | F | F |

TABLE 7-continued

Fertility of eggs from chickens immunized with goose IPVL.

| Chicken ID | Post-immunization[1] (days) | Fertility status post-laying (days) | | | | |
|---|---|---|---|---|---|---|
| | | 0 | 1 | 7 | 14 | hatch |
| 1019 | 59 | I | I | I | I | I |
| | 66 | I | I | I | I | I |
| | 68 | F | F | F | F | I |
| | 72 | F | F | F | F | F |
| 1074 | 57 | F | F | F | F | F |
| | 59 | F | F | F | F | F |
| | 60 | F | F | F | F | F |
| | 61 | F | F | F | F | F |
| | 62 | F | F | F | F | F |
| | 63 | F | F | F | F | F |
| | 65 | F | F | F | F | F |
| | 66 | F | F | F | F | F |
| | 67 | F | F | F | F | F |
| | 68 | F | F | F | F | F |
| | 69 | F | F | F | F | F |
| | 71 | F | F | F | F | F |
| | 72 | F | I | I | I | I |
| Percent fertile | | 93 | 84 | 83 | 79 | 74 |

[1]Time post-immunization that the egg was laid.
F = fertile; I = infertile; — = not determined

TABLE 8

Fertility of eggs from chickens immunized with duck IPVL.

| Chicken ID | Post-immunization[1] (days) | Fertility status post-laying (days) | | | | |
|---|---|---|---|---|---|---|
| | | 0 | 1 | 7 | 14 | hatch |
| 1049 | 56 | F | I | I | I | I |
| | 58 | F | F | F | F | F |
| | 59 | F | F | F | F | F |
| | 60 | F | F | F | F | — |
| | 62 | F | F | F | I | I |
| | 63 | F | F | F | F | F |
| | 64 | F | F | F | F | F |
| | 65 | F | I | I | I | I |
| | 66 | F | F | F | F | F |
| | 68 | I | I | I | I | — |
| | 69 | F | F | F | F | F |
| | 72 | F | I | I | I | I |
| 1031 | 56 | I | I | I | I | I |
| | 58 | F | F | F | F | F |
| | 59 | F | I | I | I | I |
| | 61 | I | I | I | I | I |
| | 62 | F | F | F | I | I |
| | 64 | F | I | I | I | I |
| | 66 | F | F | F | F | F |
| | 68 | F | I | I | I | I |
| | 70 | I | I | I | I | I |
| | 72 | I | I | I | I | I |
| 1093 | 56 | F | F | F | F | F |
| | 58 | F | F | F | F | F |
| | 59 | F | F | F | F | F |
| | 60 | F | F | F | F | F |
| | 62 | F | I | I | I | I |
| | 63 | F | F | F | F | F |
| | 65 | F | F | F | F | F |
| | 66 | F | F | F | F | F |
| | 68 | F | F | F | F | F |
| | 69 | I | I | I | I | I |
| | 72 | I | I | I | I | I |
| 695 | 56 | F | F | F | F | F |
| | 57 | F | I | I | I | I |
| | 59 | F | F | F | F | F |
| | 60 | F | F | F | F | F |
| | 63 | F | F | F | F | F |
| | 64 | F | F | F | F | F |

TABLE 8-continued

Fertility of eggs from chickens immunized with duck IPVL.

| Chicken ID | Post-immunization[1] (days) | Fertility status post-laying (days) | | | | |
|---|---|---|---|---|---|---|
| | | 0 | 1 | 7 | 14 | hatch |
| | 65 | F | F | F | F | F |
| | 67 | F | F | F | F | F |
| | 69 | F | I | I | I | I |
| | 72 | F | F | F | F | F |
| 1032 | 57 | I | I | I | I | I |
| | 60 | F | F | F | F | F |
| | 70 | F | F | F | F | F |
| | 72 | F | I | I | I | I |
| 1026 | 56 | F | F | F | F | F |
| | 57 | F | F | F | I | I |
| | 59 | F | F | F | F | F |
| | 61 | I | I | I | I | I |
| | 63 | F | I | I | I | I |
| | 64 | F | F | F | I | I |
| | 66 | F | F | F | F | F |
| | 67 | F | F | F | F | F |
| | 69 | F | F | F | F | F |
| | 70 | F | F | F | F | F |
| | 72 | F | F | F | F | F |
| 637 | 57 | I | I | I | I | I |
| | 58 | F | F | F | F | F |
| | 60 | I | I | I | I | I |
| | 61 | F | F | F | I | I |
| | 62 | F | F | F | F | F |
| | 63 | F | F | F | F | F |
| | 64 | F | F | F | F | F |
| | 65 | F | F | F | F | F |
| | 66 | F | F | F | F | F |
| | 69 | I | I | I | I | I |
| | 72 | I | I | I | I | I |
| | 72 | I | I | I | I | I |
| Percent fertile | | 80 | 64 | 64 | 56 | 48 |

[1]Time post-immunization that the egg was laid.
F = fertile; I = infertile; — = not determined

TABLE 9

Binding of chicken anti-goose IPVL and chicken anti-duck IPVL sera[1] to chicken IPVL.

| Chicken ID | Binding to chicken IPVL (as % of binding to homologous antigen) |
|---|---|
| 1179 | 1.6 |
| 1012 | 3.5 |
| 639 | 7.3 |
| 690 | 6.3 |
| 1049 | 5.2 |
| 1093 | 3.6 |
| 650 | 1.0 |
| 695 | 3.8 |
| 1032 | 0.0 |

[1]Chicken anti-goose IPVL and anti-duck IPVL sera were collected 72 days post-immunization.

We claim:

1. An immunocontraceptive vaccine composition in a liposome formulation comprising an antigen from an inner perivitelline layer (IPVL) of a bird egg, together with a pharmaceutically acceptable diluent or carrier, for preventing fertilization in a bird.

2. The immunocontraceptive vaccine composition according to claim 1, which further comprises an adjuvant.

3. The immunocontraceptive vaccine composition according to claim 2, wherein the adjuvant is Freund's complete adjuvant (FCA).

4. The immunocontraceptive vaccine composition according to claim 1, wherein the liposome comprise L-$\alpha$-lecithin (soybean) and cholesterol.

5. The immunocontraceptive vaccine composition according to claim 1, wherein a portion of the inner perivitelline layer (IPVL) is encapsulated in the liposome.

6. The immunocontraceptive vaccine composition according to claim 1, wherein the inner perivitelline layer (IPVL) is derived from a species selected from the group consisting of chicken, duck and goose.

7. The immunocontraceptive vaccine composition according to claim 6, wherein when the species is a chicken, the antigen is a 45,000 Da protein, a 48,000 Da protein or both.

8. The immunocontraceptive vaccine composition according to claim 1, wherein the bird is a chicken.

9. The immunocontraceptive vaccine composition according to claim 1, wherein the bird is a Canada goose.

10. The immunocontraceptive vaccine composition according to claim 1, wherein the bird is a snow goose.

11. A method of preventing fertilization in a bird, which comprises administering to a bird an effective amount of the immunocontraceptive vaccine composition according to claim 1.

12. The method according to claim 11, wherein administration is intramuscular.

13. An immunocontraceptive vaccine composition comprising:

(a) liposomes;

(b) an antigen from an inner perivitelline layer (IPVL) of a bird egg encapsulated in said liposomes; and (c) a pharmaceutically acceptable diluent or carrier.

14. The immunocontraceptive vaccine composition according to claim 13, further comprising an adjuvant.

15. The immunocontraceptive vaccine composition according to claim 13, wherein said liposomes comprise L-$\alpha$-lecithin (soybean) and cholesterol.

16. The immunocontraceptive vaccine composition according to claim 13, Wherein the inner perivitelline layer (IPVL) is derived from a species selected from the group consisting of chicken, duck and goose.

17. The immunocontraceptive vaccine composition according to claim 16, wherein said species is a chicken, and wherein the antigen is a 45,000 Da protein, a 48,000 Da protein or both.

18. The immunocontraceptive vaccine composition according to claim 13, wherein the bird is a chicken.

19. The immunocontraceptive vaccine composition according to claim 13, wherein the bird is a Canada goose.

20. The immunocontraceptive vaccine composition according to claim 13, wherein the bird is a snow goose.

21. A method of preventing fertilization in a bird, which comprises administering to a bird an effective amount of the immunocontraceptive vaccine composition according to claim 13.

22. The method according to claim 21, wherein administration is intramuscular.

* * * * *

UNITED STATES PATENT AND TRADEMARK OFFICE
CERTIFICATE OF CORRECTION

PATENT NO. : 6,790,457 B1
APPLICATION NO. : 09/868983
DATED : September 14, 2004
INVENTOR(S) : Robert Brown et al.

It is certified that error appears in the above-identified patent and that said Letters Patent is hereby corrected as shown below:

The following U.S. patents listed on an Information Disclosure Statement were omitted from the References Cited Section of the cover page of the U.S. Patent:

5,283,185 - 2-1994 Epand, et al
5,527,924 - 6-1996 Nantz, et al
5,656,488 - 8-1997 Curtiss III, et al
5,736,141 - 9-1998 Brown, et al The following Foreign Patent Documents listed on an Information Disclosure Statement were omitted from the References Cited Section of the cover page of the U.S. Patent:

0187702 - 7-1986 EP
9011092 - 10-1990 WO
9115501 - 10-1991 WO
9212247 - 7-1992 WO
9325231 - 10-1995 WO
9526356 - 10-1995 WO

The following Other Art listed on an Information Disclosure Statement were omitted from the References Cited Section of the cover page of the U.S. Patent:

MacKenzie, D. (1996) "Can we make supersalon safe?" New Scientist pp. 14-15.

Struzik, E. (1998) "The snow geese dilemma." Equinox 97:50-57

Column 5, line 48, "ION" should read --INVENTION--

Column 9, line 49, "Measurement of" should start on a new paragraph.

Column 11, lines 8 to 10, " [Titer (% of reference serum)¹ / TH-2P used in ELISA assay] " should read " [Titer (% of reference serum)¹ / -- / -- / TH-2P used in ELISA assay] "

UNITED STATES PATENT AND TRADEMARK OFFICE
CERTIFICATE OF CORRECTION

PATENT NO. : 6,790,457 B1  
APPLICATION NO. : 09/868983  
DATED : September 14, 2004  
INVENTOR(S) : Robert Brown et al.

Page 2 of 3

It is certified that error appears in the above-identified patent and that said Letters Patent is hereby corrected as shown below:

Column 11, lines 34 to 37, " [table image] " should read

| Vaccine TH-ZP | TH-ZP used in ELISA assay | | |
|---|---|---|---|
| | smelt | herring | perch |
| smelt | 3 | 1 | 0 |

Titer (% of reference serum)[1]

Column 11, lines 51 to 55, " [table image] " should read

| TH-ZP used in ELISA | anti-herring TH-ZP | | anti-haddock TH-ZP | |
|---|---|---|---|---|
| | rainbow trout | rabbit | rainbow trout | rabbit |

Titer (% of homologous serum)[1]

Column 13, lines 58 to 61, " [table image] " should read

| Chicken ID | Treatment[1] | (% of reference serum) Post-immunization (days) | | |
|---|---|---|---|---|
| | | 0 | 45 | 72 |

Anti-IPVL titres

Column 15, lines 21 to 22, " [table image] " should read

| | 72 | F 98 | F 88 | F 88 | F 86 | F 82 |
|---|---|---|---|---|---|---|
| Percent fertile | | | | | | |

Column 16, lines 23 to 24, " [table image] " should read

| | 72 | F 93 | 84 | 83 | 79 | 74 |
|---|---|---|---|---|---|---|
| Percent fertile | | | | | | |

UNITED STATES PATENT AND TRADEMARK OFFICE
CERTIFICATE OF CORRECTION

PATENT NO. : 6,790,457 B1
APPLICATION NO. : 09/868983
DATED : September 14, 2004
INVENTOR(S) : Robert Brown et al.

It is certified that error appears in the above-identified patent and that said Letters Patent is hereby corrected as shown below:

Column 17, lines 33 to 34, " [table image] " should read -- [table image] --

Column 18, line 42, "...Wherein..." should read -- ...wherein...--

Signed and Sealed this

Twenty-second Day of July, 2008

JON W. DUDAS
*Director of the United States Patent and Trademark Office*